US012779132B2

(12) United States Patent
Holmqvist et al.

(10) Patent No.: US 12,779,132 B2
(45) Date of Patent: Nov. 3, 2026

(54) NEEDLE SHIELD REMOVER AND A MEDICAMENT DELIVERY DEVICE COMPRISING THE NEEDLE SHIELD REMOVER

(71) Applicant: SHL MEDICAL AG, Zug (CH)

(72) Inventors: Anders Holmqvist, Värmdö (SE); Pär Leander, Nacka (SE)

(73) Assignee: SHL Medical AG, Zug (CH)

( * ) Notice: Subject to any disclaimer, the term of this patent is extended or adjusted under 35 U.S.C. 154(b) by 338 days.

(21) Appl. No.: 18/514,349

(22) Filed: Nov. 20, 2023

(65) Prior Publication Data

US 2024/0082504 A1 Mar. 14, 2024

Related U.S. Application Data

(63) Continuation of application No. 17/948,358, filed on Sep. 20, 2022, now Pat. No. 11,850,408, which is a (Continued)

(51) Int. Cl.

*A61M 5/32* (2006.01)
*A43B 13/04* (2006.01)
(Continued)

(52) U.S. Cl.

CPC ........ *A61M 5/3204* (2013.01); *A61M 5/3202* (2013.01); *A61M 5/3205* (2013.01); *A43B 13/04* (2013.01); *B29B 17/0042* (2013.01); *B29B 17/0404* (2013.01); *B29K 2023/16* (2013.01); *B29K 2075/00* (2013.01); *B29K 2105/0038* (2013.01); *B29K 2105/24* (2013.01); *B29L 2031/10* (2013.01); *B29L 2031/504* (2013.01);
(Continued)

(58) Field of Classification Search

CPC .............. A61M 5/3204; A61M 5/3202; A61M 5/3205; A61M 2005/3254; A61M 5/3137; A61M 5/3213; F04C 2270/0421

See application file for complete search history.

(56) References Cited

U.S. PATENT DOCUMENTS 5,167,640 A 12/1992 Balding
7,771,397 B1 8/2010 Olson
(Continued)

FOREIGN PATENT DOCUMENTS

CN 103974734 A 8/2014
CN 104321102 A 1/2015
(Continued)

OTHER PUBLICATIONS

International Search Report and Written Opinion for PCT/EP2018/074238, mailed Nov. 16, 2018.

*Primary Examiner* — Wesley G Harris
(74) *Attorney, Agent, or Firm* — McDonnell Boehnen Hulbert & Berghoff LLP

(57) ABSTRACT

A needle shield remover for a medicament delivery device is presented that has a metal tubular body, a proximal part, a distal part, and a substantially circular cross-section, where the tubular body is arranged with a slot extending from a distal end of the body, at least half the length of the body, towards a proximal end, such that at least the distal part of the body may flex radially outwards to exert a radially inwardly directed clamping force on a needle shield accommodated by the body.

15 Claims, 9 Drawing Sheets

Related U.S. Application Data continuation of application No. 16/759,999, filed as application No. PCT/EP2018/074238 on Sep. 10, 2018, now Pat. No. 11,497,858.

(51) Int. Cl.

| | |
|---|---|
| *B29B 17/00* | (2006.01) |
| *B29B 17/04* | (2006.01) |
| *B29K 23/00* | (2006.01) |
| *B29K 75/00* | (2006.01) |
| *B29K 105/00* | (2006.01) |
| *B29K 105/24* | (2006.01) |
| *B29L 31/10* | (2006.01) |
| *B29L 31/50* | (2006.01) |
| *C08L 23/16* | (2006.01) |
| *E04B 1/90* | (2006.01) |
| *E04C 1/40* | (2006.01) |
| *E04C 2/26* | (2006.01) |

(52) U.S. Cl.

CPC .......... *C08L 23/16* (2013.01); *C08L 2203/14* (2013.01); *C08L 2205/025* (2013.01); *C08L 2205/035* (2013.01); *C08L 2207/02* (2013.01); *C08L 2207/04* (2013.01); *C08L 2207/062* (2013.01); *E04B 1/90* (2013.01); *E04C 1/40* (2013.01); *E04C 2/26* (2013.01)

(56) References Cited

U.S. PATENT DOCUMENTS

| | | | |
|---|---|---|---|
| 2016/0175539 | A1 | 6/2016 | Riedel et al. |
| 2016/0354551 | A1 | 12/2016 | Keim et al. |
| 2017/0274151 | A1 | 9/2017 | Allen |

FOREIGN PATENT DOCUMENTS

| | | | | |
|---|---|---|---|---|
| EP | 2255842 | A1 | 12/2010 | |
| EP | 2361648 | A1 | 8/2011 | |
| EP | 2468328 | A1 | 6/2012 | |
| EP | 2878322 | A1 | 6/2015 | |
| EP | 2886144 | A1 | 6/2015 | |
| EP | 3222313 | A1 | 9/2017 | |
| GB | 2541445 | A | 2/2017 | |
| TW | 201722489 | A | 7/2017 | |
| TW | 201722493 | A | 7/2017 | |
| WO | 2009090499 | A1 | 7/2009 | |
| WO | 2010007395 | A1 | 1/2010 | |
| WO | 2011101379 | A1 | 8/2011 | |
| WO | 2012/103140 | A1 | 8/2012 | |
| WO | WO-2013058697 | A1 * | 4/2013 | .......... A61M 5/3202 |
| WO | WO-2014091153 | A1 * | 6/2014 | .......... A61M 5/3204 |
| WO | 2015/110532 | A1 | 7/2015 | |
| WO | 2016089864 | A1 | 6/2016 | |
| WO | 2016193353 | A1 | 12/2016 | |

* cited by examiner

NEEDLE SHIELD REMOVER AND A MEDICAMENT DELIVERY DEVICE COMPRISING THE NEEDLE SHIELD REMOVER

CROSS REFERENCE TO RELATED APPLICATIONS

The present application is a continuation of U.S. patent application Ser. No. 17/948,358, filed Sep. 20, 2022, which is a continuation of U.S. patent application Ser. No. 16/759,999, filed Apr. 28, 2020, now U.S. Pat. No. 11,497,858, which is a U.S. National Phase Application pursuant to 35 U.S.C. § 371 of International Application No. PCT/EP2018/074238 filed Sep. 10, 2018, which claims priority to European Patent Application No. 17200475.6 filed Nov. 7, 2017. The entire disclosure contents of these applications are herewith incorporated by reference into the present application.

TECHNICAL FIELD

The present disclosure relates to a needle shield remover and in particular to a needle shield remover having a radially flexible body.

BACKGROUND

Today's medicament delivery devices may be complex and involve many different components. The more components comprised in a device, the more complicated and costly it becomes. It is therefore necessary to minimize the number of components and to reduce the cost and complexity of each individual component.

The present disclosure relates to one such component, namely to a needle shield remover. The needle shield remover is often assembled with a cap, or closure member, of a medicament delivery device and is engaged to a needle shield, which protects a needle by hermetically enclosing it. The shield may comprise a flexible rubber member in which the needle is embedded, i.e. a flexible needle shield (FNS). For some applications, the FNS is provided with a rigid outer shell, i.e. a rigid needle shield (RNS). To be able to remove the needle shield before use of the medicament delivery device, the needle shield remover is provided with gripping members that engage the needle shield. Since the needle shield remover is attached to the cap, removal of the cap will also pull away the needle shield from the needle, due to the gripping members' engagement with the needle shield.

A conventional needle shield remover is disclosed in EP2255842, wherein a cap (manually operable member) comprises a needle shield remover (tubular shaped member), which surrounds a RNS. Flexible gripping members are arranged in the needle shield remover to engage the RNS such that when a user pulls the cap off a medicament delivery device, the needle shield remover will grip the RNS and pull it off an injection needle, thereby making the device ready for delivery of a dose of medicament.

However, the needle shield remover of the referenced prior art device suffers from the fact that it is costly, because it is formed out of a seamless stainless steel tube. In addition, the prior art device relies on the relatively weak resilient force of the flexible gripping members to engage the RNS and dislodge it from the injection needle—an operation which may require considerable force. The prior art gripping members may also rely on good tolerances for the gripping members to engage certain areas of the RNS, such as depressions in the outer circumferential surface, or the rear edge of the RNS. Since the position of the RNS relative to the needle shield remover may vary depending on tolerances of the glass container. The position may also depend on the handling of the delivery device since the container and its needle shield may move inside the delivery device, for instance due to accidental impacts. If the position of the needle shield is not correct, the prior art gripping members may not be able to engage the needle shield, which will result in the needle shield still being attached to the needle and to the container when the cap is removed from the housing.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

In view of the background outlined above, a general object of the present disclosure is to provide a needle shield remover for a medicament delivery device, which needle shield remover is radially flexible and may exert a radial clamping force on a needle shield accommodated therein.

According to a main aspect of the disclosure it is characterised by a needle shield remover for a medicament delivery device, which needle shield remover comprises a metal tubular body, having a proximal part, a distal part, and a substantially circular cross-section, the tubular body being arranged with a slot extending from a distal end of the body, at least half the length of the body, towards a proximal end, such that at least the distal part of the body may flex radially outwards to exert a radially inwardly directed clamping force on a needle shield accommodated in the body.

An inner radius of the tubular body is equal to or smaller than an outer radius of a needle shield. Therefore, the tubular body of the needle shield remover will flex radially outwards when the needle shield is inserted in the body, such that the body exerts a radial clamping force on the needle shield. The clamping force may be selected, as deemed appropriate, as a function of the inner radius of the body in relation to the outer radius of the needle shield. A smaller inner radius of the body results in a greater clamping force.

According to another object of the present disclosure an inner diameter of at least the distal part of the body, in a relaxed state, is smaller than an outer diameter of the needle shield that is to be accommodated by the body.

Due to the inner diameter of the body being smaller than the outer diameter of the needle shield, the body, or at least the distal part of the body, needs to flex radially outwards, i.e. to expand, to make room for the needle shield. When the needle shield is in place, i.e. accommodated in the body, the body will seek to return to the relaxed state and thereby exerts a radially inwardly directed clamping force on the needle shield.

According to another object of the present disclosure the body is formed of a rolled metal sheet.

A rolled metal sheet is preferable to a tube in that it is easier and less expensive to manufacture the needle shield remover from a sheet than from a tube. It will also naturally provide the inwardly directed clamping force when it is flexed radially outwards.

According to another object of the present disclosure the slot is formed of a gap between substantially parallel opposing edges of the rolled metal sheet.

An advantage of the rolled metal sheet is that the slot is formed by the space between the substantially parallel opposing edges of the metal sheet which is rolled to form the tubular body of the needle shield remover. The radial clamping force that is used to engage the needle shield is configured by adapting the diameter of the rolled body in relation to the diameter of the needle shield that is to be removed. A smaller diameter of the body results in a greater clamping force on the needle shield.

According to another object of the present disclosure the opposing edges of the proximal part of the body are arranged with mutually engaging structures such as to prevent radial flexing of the proximal part of the body when the distal part of the body flexes radially due to accommodation of a needle shield therein.

In order to stabilise the proximal part of the body at the connection with the cap, the metal sheet may be provided with an engaging structure, such as a positive connection, e.g. a jigsaw shape, at the proximal part of the body. The opposing edges of the proximal part of the body may thereby be attached to each other to provide the proximal part of the tubular body with a rigid diameter.

According to another object of the present disclosure a transversal cut-out intersects the slot between the proximal part and the distal part to reduce radial flexing of the proximal part of the body when the distal part of the body flexes radially due to accommodation of a needle shield therein.

An alternative, or additional, solution is thereby provided to stabilise the proximal part of the tubular body by mechanically isolating the proximal part from the radial flexing of the distal part. The transversal slot intersects the longitudinal slot such that the radial forces resulting from the expansion of the distal part, as the needle shield remover accommodates the needle shield, are isolated and reduce the radial expansion forces on the proximal part.

According to another object of the present disclosure the slot is formed as a partial cut-out from a distal end of a wall of a metal tube such that the proximal part of the body is radially rigid and the distal part of the body is radially flexible.

A metal tube may be utilised to form the body by cutting a substantially longitudinal slot in a tubular wall of the tube, from the distal end of the tube towards the proximal end, but leaving a proximal part of the tube intact. A distal part of the tube forms the distal part of the body and is radially flexible to provide a radial clamping force, whereas the proximal part of the tube forms the proximal part of the body and is substantially radially rigid, or inflexible. The rigid proximal part provides a more reliable attachment of the needle shield remover to a cap of the medicament delivery device.

According to another object of the present disclosure rigid gripping members protrude radially inwards from the distal part of the body.

The rigid gripping members are relatively strong and mechanically resistant in relation to conventional, flexible, gripping members. The radially inwardly directed clamping force of the body urges the rigid gripping members into contact with a needle shield accommodated in the body. By comparison, conventional, flexible, gripping members would be pressed flat against the needle shield due to the radial clamping force of the body of the needle shield remover. Consequently, flexible gripping members would not be able to engage an outer surface of the needle shield.

According to another object of the present disclosure the rigid gripping members are formed as radially inwardly directed punched structures, having proximally directed edges to enhance friction between the body and a needle shield accommodated in the body, when the body is proximally urged.

The inwardly directed structures, having proximally directed edges, comprise holes punched out of the metal body, and the rim, or edge, of each hole is a relatively sharp lip that provides a frictional engagement with the outer surface of the needle shield accommodated in the body. Accordingly, an increased clamping force of the body of the needle shield remover also increases said frictional engagement since the gripping members are rigid and do not deform under the clamping force of the body.

According to another object of the present disclosure the proximal part of the tubular body is arranged with an attachment structure for connecting the needle shield remover to a cap of a medicament delivery device.

The tubular body forms the needle shield remover, which may be attached to a cap of a medicament delivery device, such that removal of the cap results in the removal of a needle shield that covers an injection needle of the medicament delivery device.

According to another object of the present disclosure the attachment structure comprises a circumferential groove formed in the tubular body.

A circumferential groove may be snap-fitted with a corresponding attachment structure of the cap.

According to another object of the present disclosure the attachment structure comprises radially outwardly directed tongues formed by cut-outs of the proximal end of the tubular body.

Tongues may be cut in the proximal end of the tubular body. The tongues are especially simple to cut and to bend in the metal sheet, which is thereafter rolled to form the tubular body.

According to another object of the present disclosure the attachment structure comprises a radially outwardly directed flange.

The proximal end of the body may also be formed as a radially outwardly directed flange, i.e. forming the attachment structure without tongues.

According to further object of the present disclosure a medicament delivery device comprises a needle shield remover according to any of the previous embodiments.

DETAILED DESCRIPTION

Figure 1:
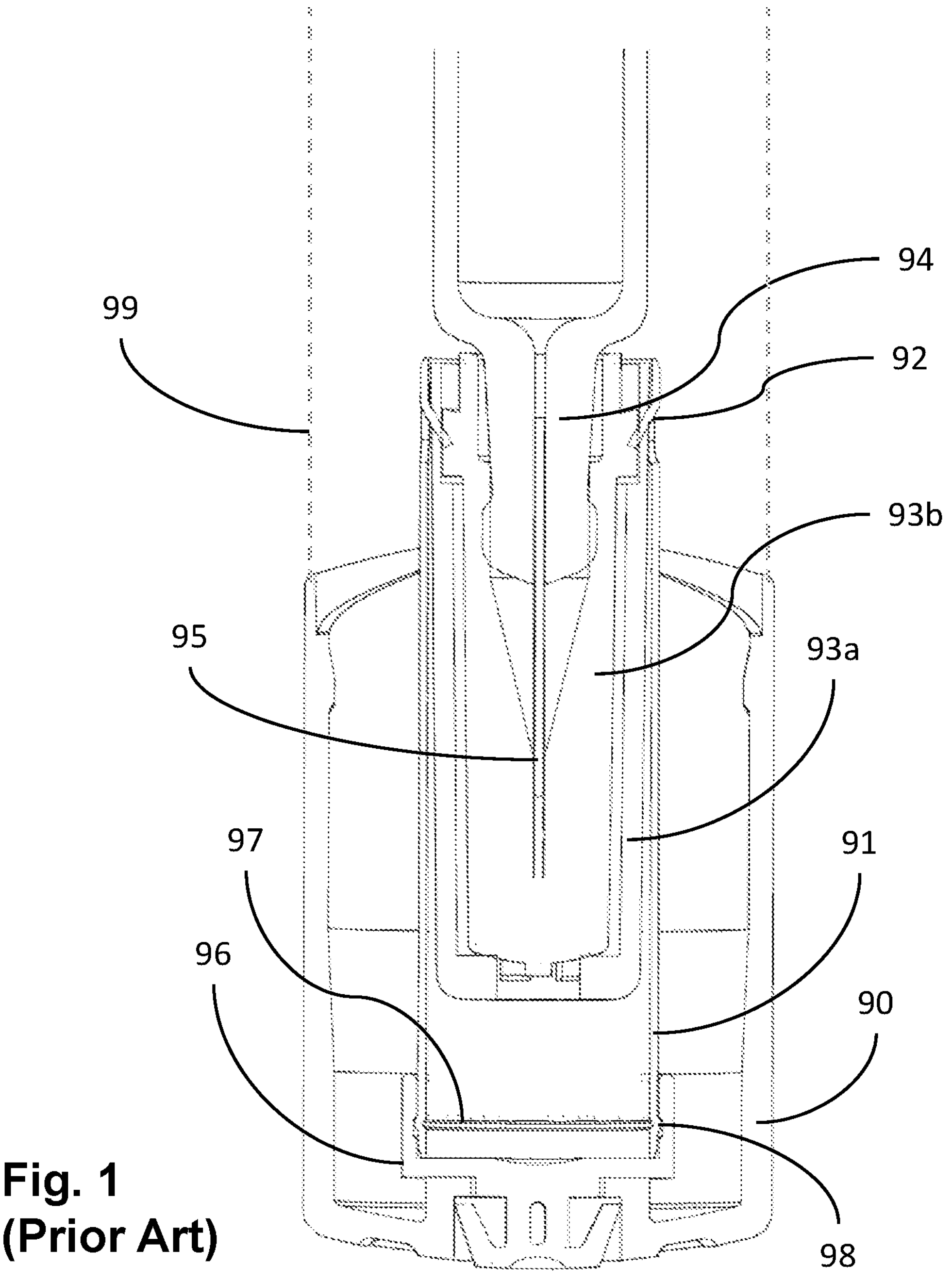
Fig. 1 (Prior Art)
FIG. 1 is a cross-sectional view of a prior art cap, needle shield remover, and syringe.

FIG. 1 shows a cross-sectional view of a known cap and needle shield remover. A needle 95 is fixedly mounted in a proximal end of a container 94, such as a glass syringe. The syringe is accommodated in a housing 99 of a medicament delivery device. A generally tubular cap 90 is assembled with a tubular needle shield remover 91 via a connection, where a mutual circumferential groove-protrusion 97 of the needle shield remover, mating with a corresponding protrusion-groove 98 located in a cup 96 of the cap 90. The cap-needle shield remover assembly is removably attached to the housing 99. A flexible needle shield 93*b*, embedding the needle 95, is attached to, and accommodated in, a rigid needle shield 93*a*. The needle shield remover 91 comprises flexible gripping members 92, in the form of radially inwardly protruding tongues, which engage the needle shield 93*a* and 93*b* by protruding into holes, or depressions, in a tubular wall of the rigid needle shield 93*a*. When the medicament delivery device is to be used, a user pulls the cap 90 proximally away from the housing 99. The gripping members 92 will thereby pull the rigid needle shield 93*a* and the flexible needle shield 93*b* off the needle 95, exposing the needle 95.

As previously described, prior art needle shield removers are relatively expensive components of a medicament delivery device, because they are often manufactured from seamless stainless steel tubes, which are cut in desired lengths and provided with gripping members 92 and attachments structures, such as the groove-protrusions 97, 98. They also rely on the flexible gripping members 92 being able to engage the needle shield, either at a depression at the circumferential side surface of the needle shield, or at the distal end, i.e. a rear-facing end surface of the needle shield. Due to tolerances and an uncertain position of the container 94 in relation to the housing 99, such an engagement cannot always be assured.

An object of the present disclosure is therefore to provide a less costly and more reliable needle shield remover. Basically, the solution pertains to a needle shield remover 30 which comprises a metal tubular body 100, 200, having a proximal part A, a distal part B, and a substantially circular cross-section, the tubular body 100, 200 being arranged with a slot extending from a distal end of the body, at least half the length of the body 100, 200, towards a proximal end, such that at least the distal part B of the body may flex radially outwards to exert a radially inwardly directed clamping force on a needle shield accommodated by the body 100, 200. See FIGS. 2-6.

Figure 7A:
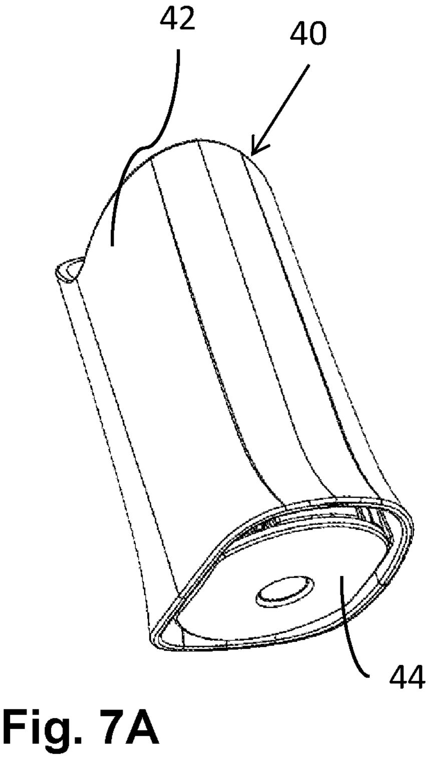
FIG. 7A is a perspective view of a cap containing a needle shield remover according to an embodiment of the present disclosure.
Figure 7B:
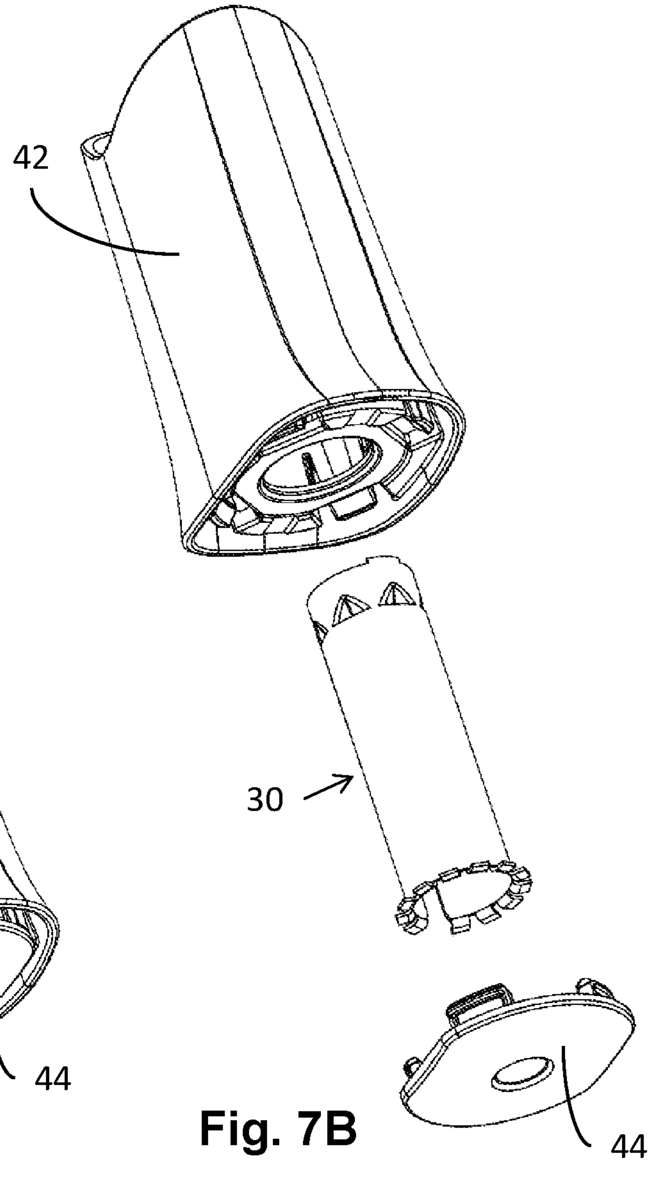
FIG. 7B is an exploded perspective view of a cap and a needle shield remover according to a third embodiment of the present disclosure.

The clamping force may be produced by ensuring that an inner diameter of at least the distal part B of the body, in a relaxed state, is smaller than an outer diameter of the needle shield that is to be accommodated by the body. Thus, when the container with its needle and needle shield are mounted in a housing of the medicament delivery device, similarly to the prior art device shown in FIG. 1, the needle shield remover 30, which is assembled with a cap 40 (FIGS. 7A and 7B), may be pushed onto the needle shield such that the distal part B of the body 100, 200 is radially expanded relative to a longitudinal axis 500. As the metal body seeks to relax towards the relaxed, non-expanded state, the radially inwardly directed clamping force is exerted on the needle shield.

The clamping force may be exploited for the employment of an improved kind of rigid gripping members 32, as compared to the flexible prior art gripping members 92. The rigid gripping members 32 protrude radially inwards from a tubular wall of the distal part B of the body 100, 200. The gripping members 32 are formed as radially inwardly directed punched structures, having proximally directed edges to enhance friction between the body 100, 200 and a needle shield accommodated in the body 100, 200, when the body is proximally urged, such as when the cap 40 is removed from the housing of the medicament delivery device by the user.

The rigid gripping members 32 are relatively strong and mechanically resistant in relation to the conventional, flexible, gripping members 92. The radially inwardly directed clamping force of the body urges the rigid gripping members 32 into contact with a needle shield accommodated in the body 100, 200. By comparison, the conventional, flexible, gripping members 92 would be pressed flat against the needle shield due to the radial clamping force of the body 100, 200 of the needle shield remover 30. Consequently, flexible gripping members 92 would not be able to engage an outer surface of the needle shield.

The inwardly directed structures, having proximally directed edges, comprise holes punched out of the metal body. The rim, or edge, of each hole has a relatively sharp lip which provides a frictional engagement with the outer surface of the needle shield accommodated in the body 100, 200. Accordingly, an increased clamping force of the body of the needle shield remover also increases the frictional engagement since the gripping members 32 are rigid and do not deform under the clamping force of the body 100, 200.

The slot 10, 20 expands, or widens, as the needle shield is accommodated in the needle shield remover 30 from the distal end of the needle shield remover 30. Usually, the needle shield does not extend the whole length of the needle shield remover 30. The main flexing movement and clamping force of the needle shield remover will therefore be exerted by the distal part B. Furthermore, the proximal part is configured to be attached to the cap 40, as will be explained below. To ensure a good attachment to the cap it may be preferable to stabilise the proximal part A, to reduce the radial flexing thereof.

Figure 8:
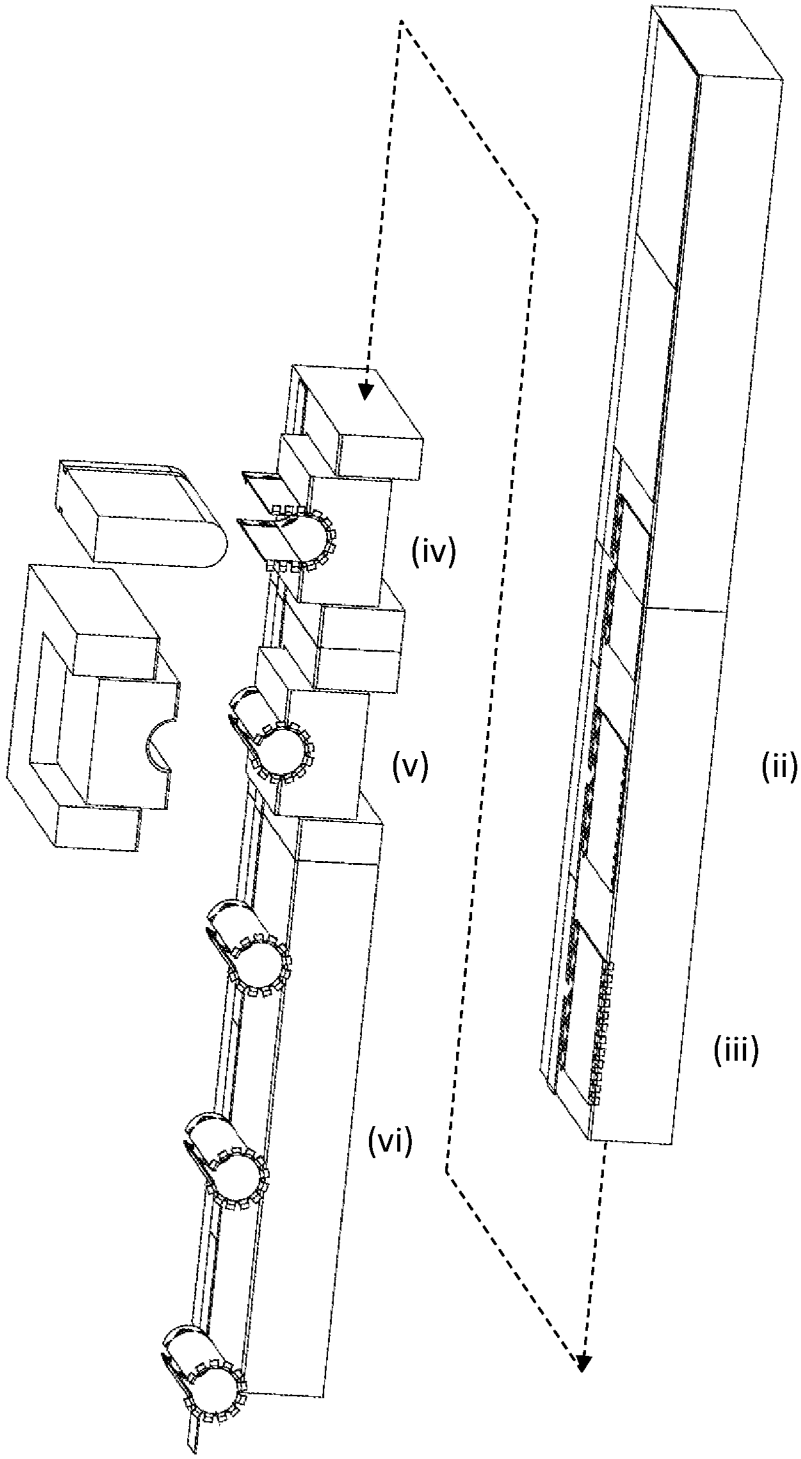
FIG. 8 is a conceptual schematic view of a possible manufacturing set-up for making the needle shield removers of the present disclosure.

In one embodiment, the body 100 is formed of a rolled metal sheet. See FIGS. 2-5. The rolled metal sheet may be formed into a tubular body in a number of simple processing steps (FIG. 8). The metal sheet tubular body 100 is therefore a less costly alternative to the seamless stainless tube 91 of prior art devices. The diameter of the body 100 is furthermore easy to set during manufacture of the body 100 to configure the appropriate clamping force.

Figure 2:
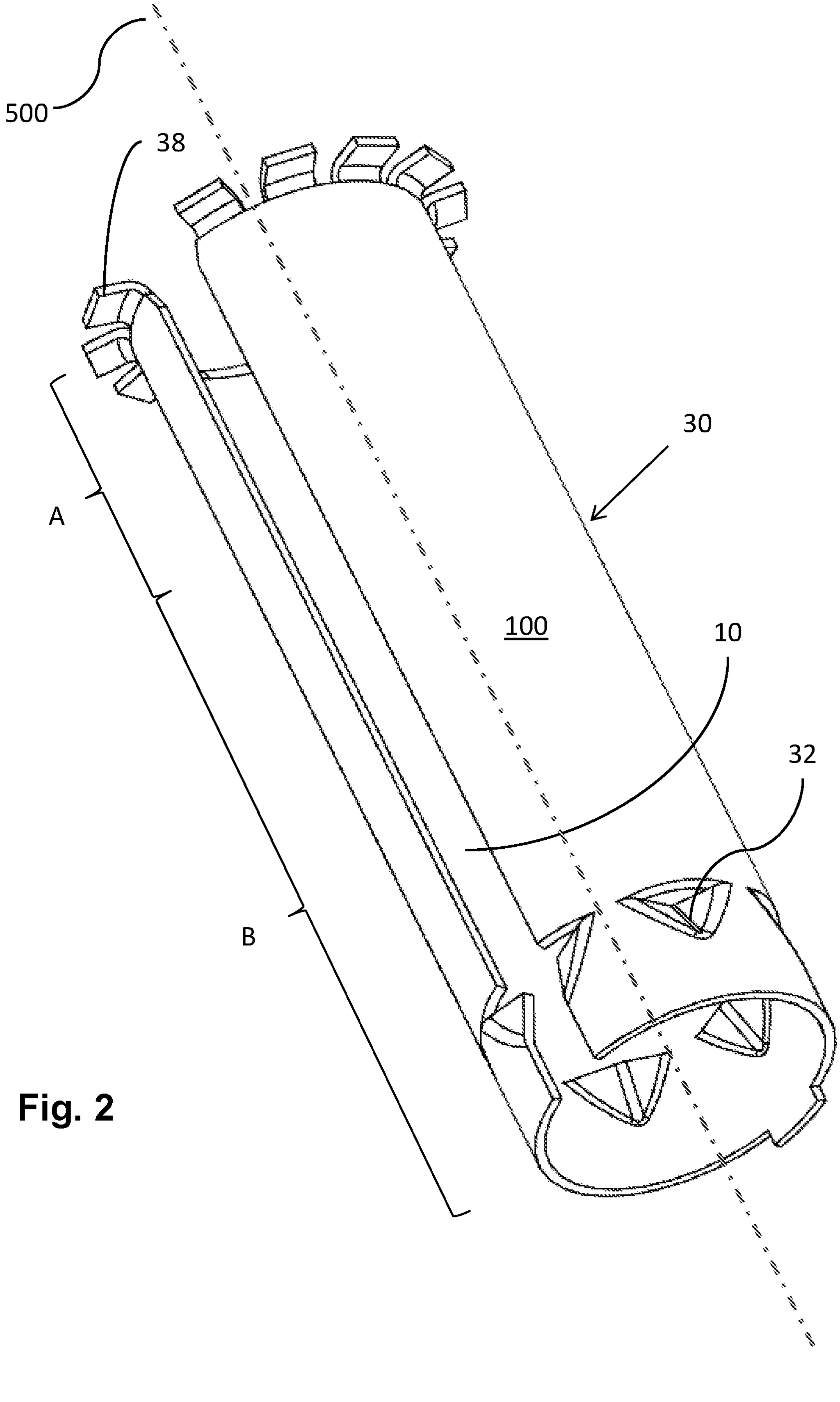
FIG. 2 is a perspective view of a needle shield remover according to a possible embodiment of the present disclosure.

The slot 10 of the rolled metal sheet tubular body is formed of a gap between substantially parallel opposing edges of the rolled metal sheet. The slot 10 extends the whole length of the body 100. Basically, the whole body may be allowed to flex radially as the needle shield is accommodated therein, without significantly affecting the attachment of the cap 40 at the proximal part A of the body 100. Such a configuration is shown in FIG. 2.

Figure 3:
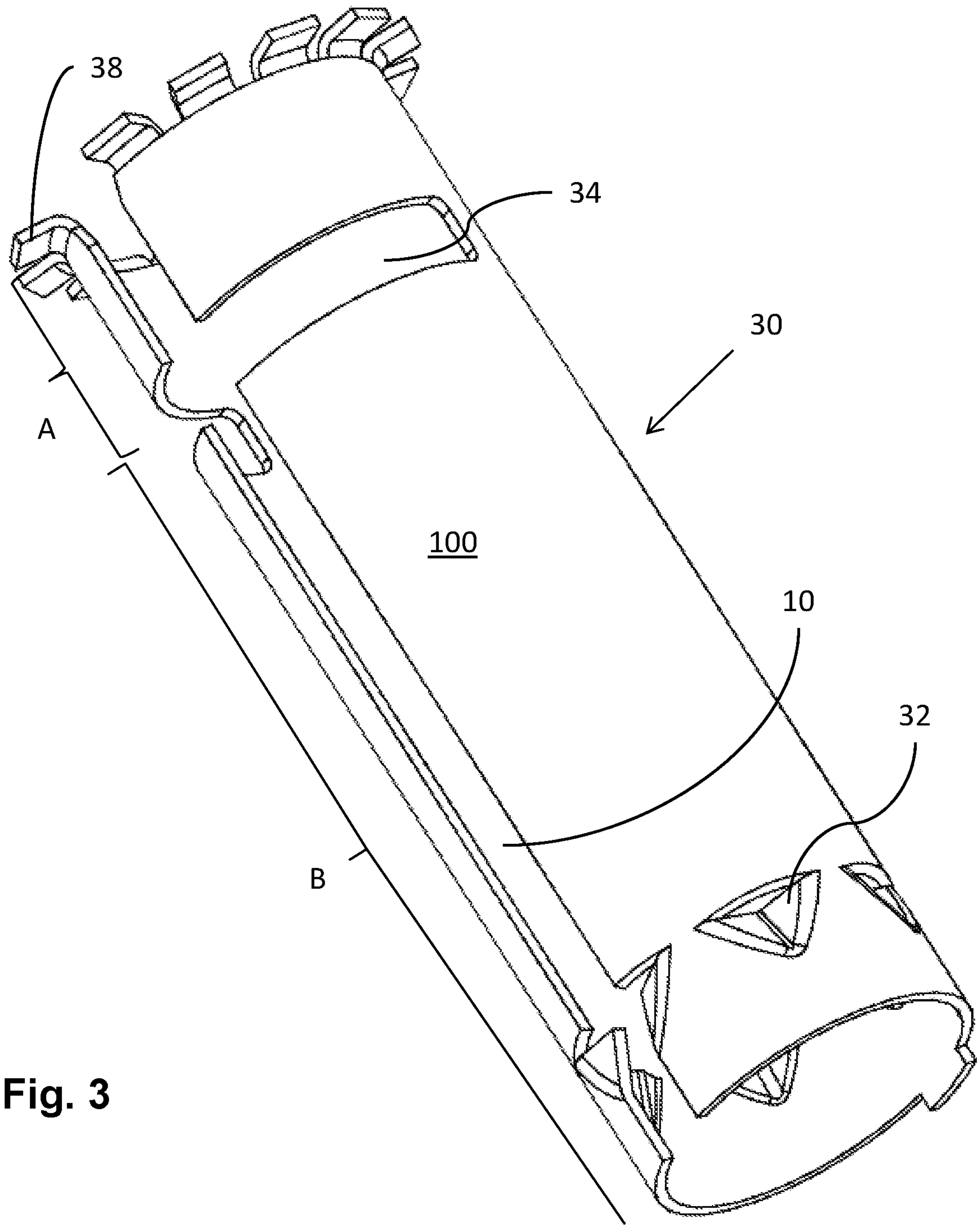
FIG. 3 is a perspective view of a needle shield remover according to another embodiment of the present disclosure.

However, if the radial flexing of the proximal part A of the body 100 is perceived as a problem, various measures may be taken to reduce the flexing in the proximal part A, as mentioned above. FIG. 3 shows the needle shield remover 30 wherein a transversal cut-out 34 intersects the slot 10 between the proximal part A and the distal part B to reduce radial flexing of the proximal part A of the body when the distal part B of the body 100 flexes radially due to accommodation of a needle shield therein. The transversal cut-out thereby relieves the proximal part A of the radial forces at work in the distal part B when accommodating the needle shield in the needle shield remover 30, which stabilises the attachment of the needle shield remover with the cap 40. The transversal cut-out may be described as two transversal cut-out arms which extend from the slot 10. Each cut-out arm preferably extends at least a quarter of the circumference of the body 100 from the slot 10.

Figure 4:
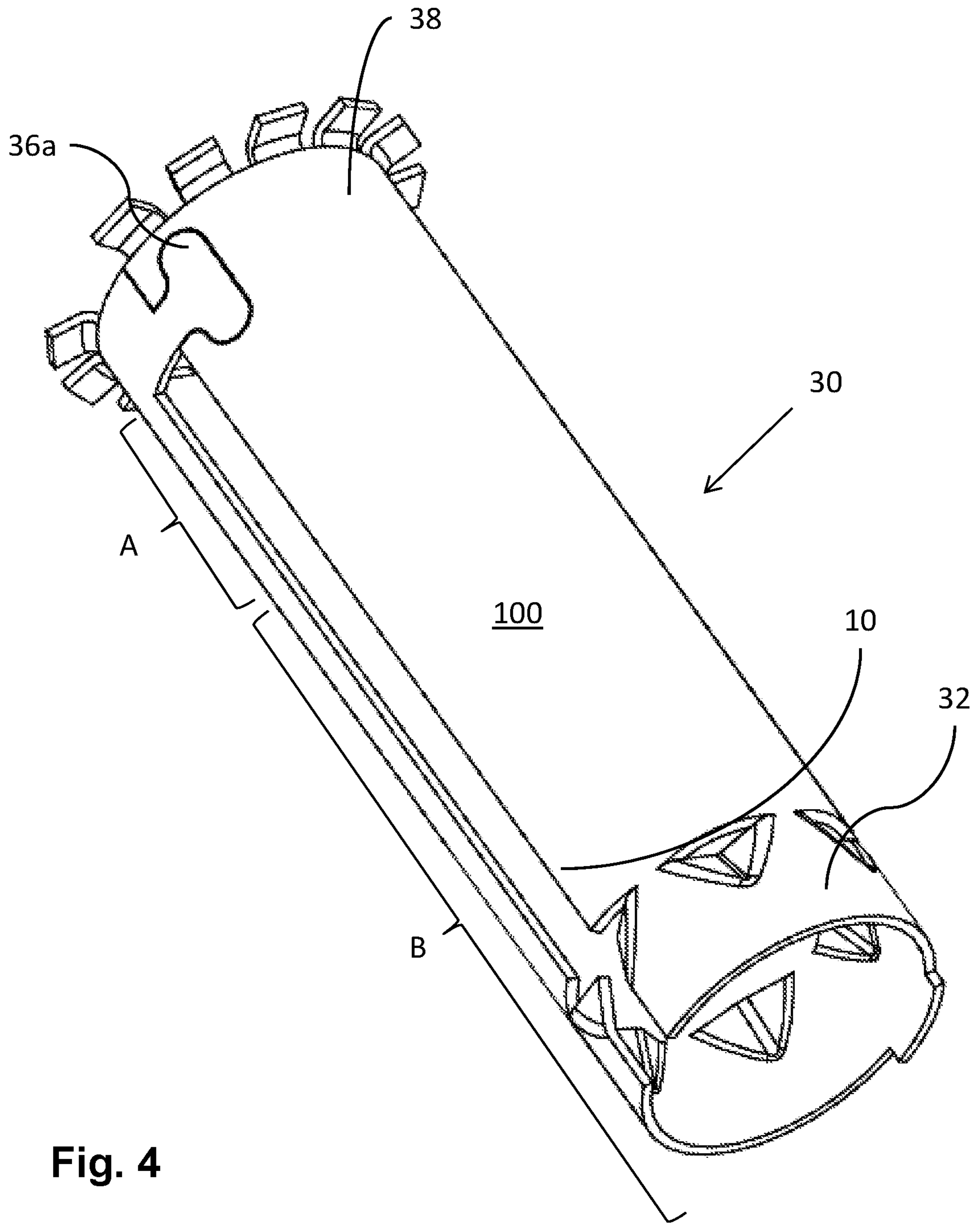
FIG. 4 is a perspective view of a needle shield remover according to yet another embodiment of the present disclosure.
Figure 5:
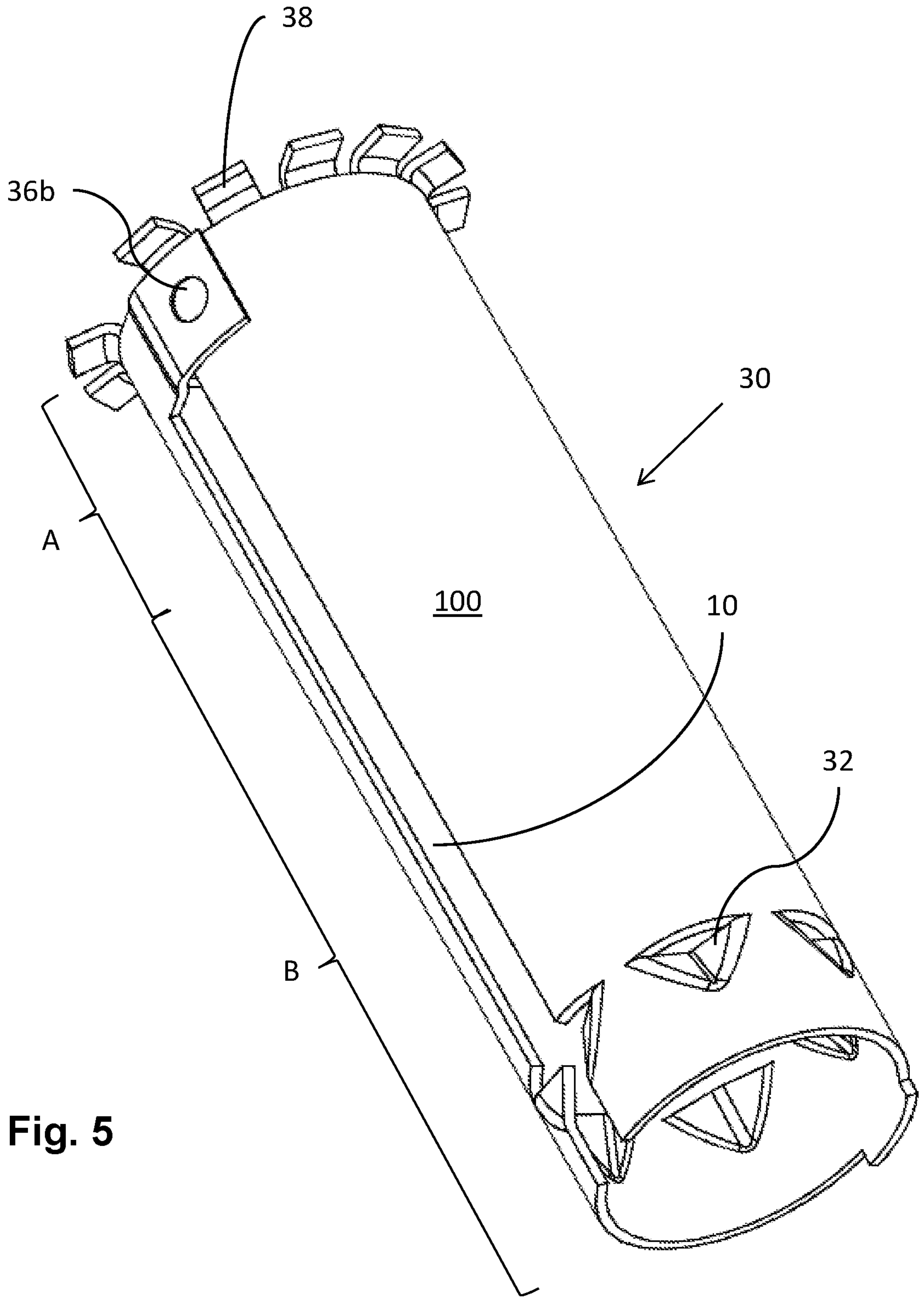
FIG. 5 is a perspective view of a needle shield remover according to still another embodiment of the present disclosure.

An alternative solution is shown in FIGS. 4 and 5, wherein the opposing edges of the proximal part A of the body 100 are arranged with mutually engaging structures 36*a*, 36*b* such as to prevent radial flexing of the proximal part of the body when the distal part of the body flexes radially due to accommodation of a needle shield therein. The mutually engaging structure 36*a* (FIG. 4) is shown as a positive connection, such as a jigsaw connection 36*a*. Other forms of connections are also conceivable, such as latches, snap fits, etc. The purpose is to lock the opposing edges of the proximal part A to each other to reduce the radial flexing.

Another alternative solution to achieve the stable proximal part A, but still provide the clamping forces around the needle shield is to form the slot 20 as a partial cut-out from a distal end of a wall of a metal tube such that the proximal part A of the body 200 is radially rigid and the distal part B of the body 200 is radially flexible. See FIG. 6. Obviously, the advantage of the low-cost, rolled metal sheet is lost, but the clamping forces achieved by the slot still allow the use of the rigid gripping members 32.

Figure 6:
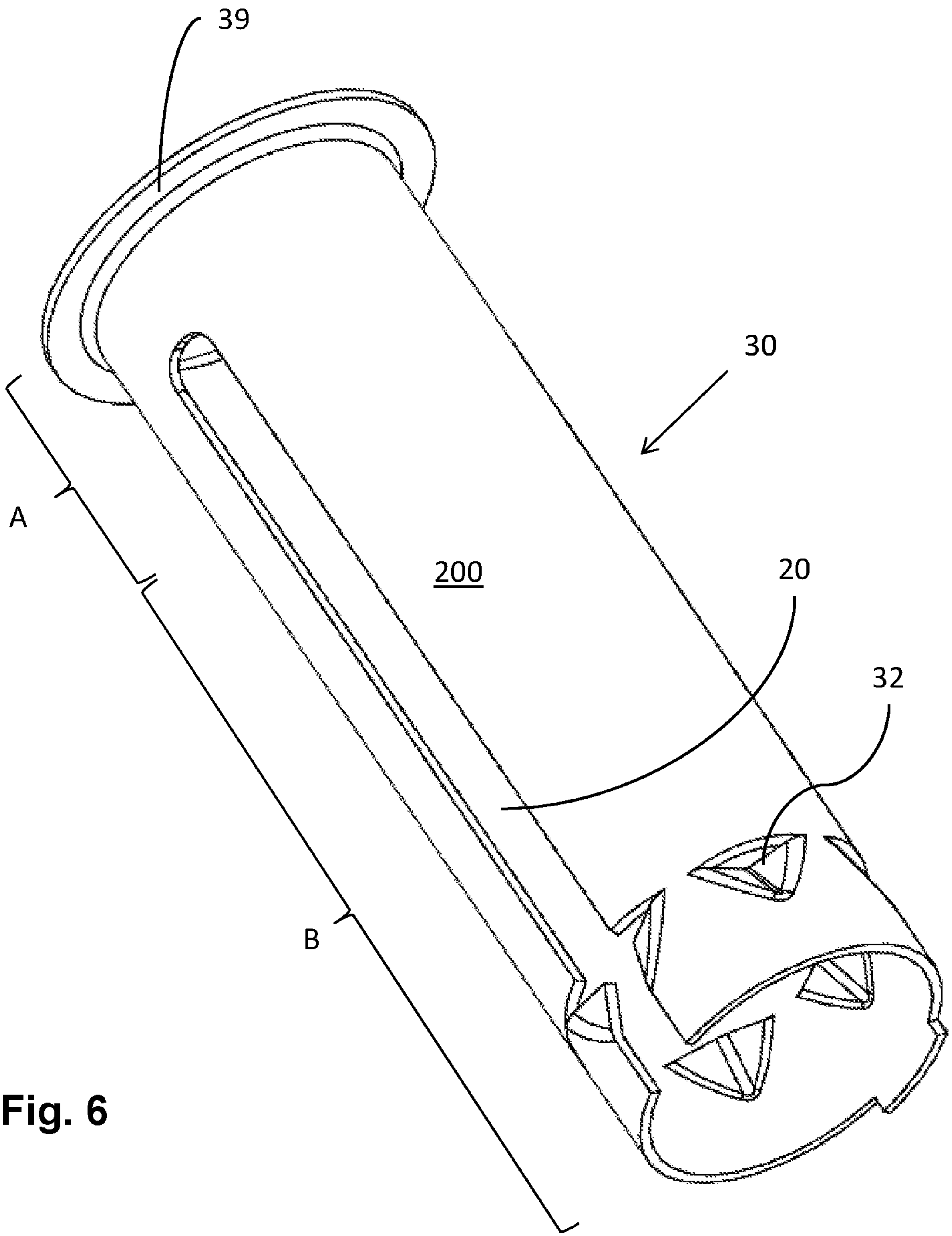
FIG. 6 is a perspective view of a needle shield remover according to yet another possible embodiment of the present disclosure.

In FIGS. 2-7, the needle shield remover 30 is shown with the body 100, 200 arranged with an attachment structure 38, 39 for connecting the needle shield remover to a cap 40 of a medicament delivery device. The attachment structure may be radially extending tongues 38 formed by cut-outs of the proximal end of the tubular body 100, 200 or a radially outwardly directed flange 39 (FIG. 6). The cap 40 may include a cap housing 42 and a lid 44 (FIGS. 7A-7B).

Figure 9:
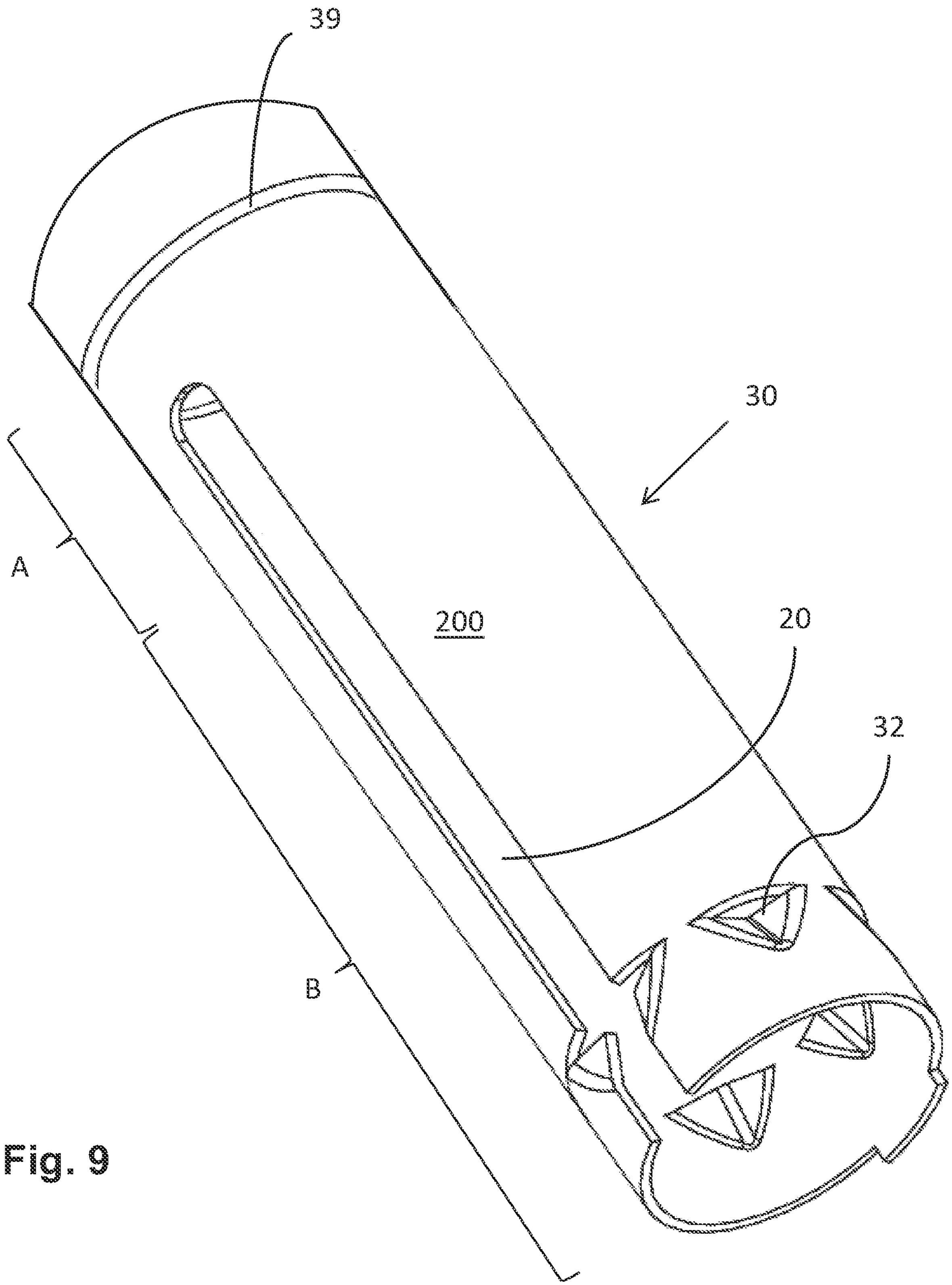
FIG. 9 is a perspective view of a needle shield remover according to yet another possible embodiment of the present disclosure.

An alternative attachments structure may be the conventional groove-protrusion structure known from prior art. An elongated protrusion along the circumferential surface of the body 100, 200 is configured to mate with an elongated groove of a corresponding attachments structure of the cap 40 in a snap-fit connection (not shown). Of course, the protrusion of the body may be exchanged for a groove as exemplified in FIG. 9, and the groove of the cap may be exchanged for a corresponding protrusion. However, the radially extending tongues 38, or flange 39, described above, are more robust to any radial flexing of the proximal part A of the needle shield remover 30.

An alternative attachments structure may be the conventional groove-protrusion structure known from prior art. An elongated protrusion along the circumferential surface of the body 100, 200 is configured to mate with an elongated groove of a corresponding attachments structure of the cap 40 in a snap-fit connection (not shown). Of course, the protrusion of the body may be exchanged for a groove, and the groove of the cap may be exchanged for a corresponding protrusion. However, the radially extending tongues 38, or flange 39, described above, are more robust to any radial flexing of the proximal part A of the needle shield remover 30.

FIG. 8 shows a conceptual view of some manufacturing steps of the needle shield remover 30 having a rolled metal sheet body 100. Metal sheets are supplied (i) and cut into preferred widths and lengths. Gripping members and attachment structures are punched in the metal sheets (ii). The attachments structures are folded (iii). The sheets are formed into half-pipes (iv), followed by shaping of the half-pipes into tubular forms (v), which concludes the fabrication of the needle shield remover (vi).

The invention claimed is:

1. A cap assembly for a medicament delivery device, the cap assembly comprising:

a cap removably attached to a proximal end of the medicament delivery device, the cap comprising a cap housing and a lid;

a needle shield remover comprising a metal tubular body having a longitudinal axis and an attachment structure located at a proximal end of the tubular body, where the attachment structure comprises a radially outwardly directed flange that is securely held inside of the cap, and where a distal part of the tubular body comprises a substantially circular cross-section, wherein a portion of the distal part of the tubular body flexes radially outwards relative to the longitudinal axis when a needle shield is positioned within the tubular body, and wherein the outward radial flexing of the portion of the distal part of the tubular body causes a simultaneous radial inward clamping force exerted by a portion of the proximal end of the tubular body on the needle shield; and a plurality of gripping members located in the distal part of the tubular body that protrude radially inwards relative to the longitudinal axis, where the gripping members are configured to engage the needle shield such that axial movement of the tubular body directly results in simultaneous axial movement of the needle shield.

2. The cap assembly of claim 1, wherein the flange is sandwiched between an inner surface of the lid and a bearing surface located inside of the cap housing.

3. The cap assembly of claim 1, wherein the flange connects directly to an inner surface of the lid when the lid is attached to a proximal part of the cap housing.

4. The cap assembly of claim 1, wherein the flange comprises a plurality of tongues.

5. The cap assembly of claim 1, wherein the flange comprises at least two tongues and a cut-out adjacent and separating the at least two tongues.

6. The cap assembly of claim 1, wherein the flange comprises tongues that are formed by cut-outs in a terminal end of the proximal end of the tubular body.

7. The cap assembly of claim 1, further comprising an engaging structure located in a proximal part of the tubular body configured to prevent outward radial flexing of the proximal part when the portion of the distal part of the tubular body flexes radially inward.

8. The cap assembly of claim 1, wherein the distal part of the tubular body comprises an inner diameter, that in a relaxed state, is smaller than an outer diameter of the needle shield that is to be accommodated by the tubular body.

9. The cap assembly of claim 1, wherein the tubular body is formed from a single rolled metal sheet.

10. The cap assembly of claim 1, wherein the tubular body further comprises parallel opposing edges of a single rolled metal sheet.

11. The cap assembly according to claim 10, wherein opposing edges of a proximal part of the tubular body are arranged with mutually engaging structures to prevent radial flexing of the proximal part of the tubular body when the distal part of the tubular body flexes radially to accommodate insertion of the needle shield.

12. The cap assembly according to claim 1, wherein the flange comprises a plurality of tongues that are formed by punching cut-outs along an edge of a single metal sheet and then folding the tongues before shaping the metal sheet into the tubular body such the tongues are generally perpendicular to the longitudinal axis.

13. A medicament delivery device comprising:
a housing comprising a needle mounted to a medicament container, where the needle is covered by a needle shield; and
a cap assembly removably attached to a proximal end of the medicament delivery device, where the cap assembly comprises:
a cap having a cap housing and a lid; and
a needle shield remover comprising a metal tubular body having a longitudinal axis and an attachment structure located at a proximal end of the tubular body, where the attachment structure comprises a radially outwardly directed flange that is securely held inside of the cap wherein:
the tubular body further comprises a plurality of gripping members located in a distal part of the tubular body that protrude radially inwards relative to the longitudinal axis, where the gripping members are configured to engage the needle shield such that axial movement of the tubular body directly results in simultaneous axial movement of the needle shield,
outward radial flexing of a portion of the distal part of the tubular body causes a simultaneous radial inward clamping force exerted by a portion of the proximal end of the tubular body on the needle shield, and
the flange is sandwiched between an inner surface of the lid and an inner surface located in a proximal part of the cap.

14. The medicament delivery device of claim 13, wherein the flange is positioned within the cap such that the cap housing and the lid can rotate relative to the tubular body but axial proximal movement of the cap housing relative to the needle shield will cause axial movement of the tubular body such that the gripping members engage the needle shield.

15. The medicament delivery device of claim 13, wherein the gripping members comprise rigid punched sheet metal structures each having a proximally directed edge.

* * * * *